US006462027B2

(12) United States Patent
Poet et al.

(10) Patent No.: US 6,462,027 B2
(45) Date of Patent: *Oct. 8, 2002

(54) DELIVERY OF NUCLEIC ACID INTO AQUATIC ANIMALS

(75) Inventors: Steven E. Poet, Winterville; Victoria Vaughn Burnley, Athens, both of GA (US)

(73) Assignee: University of Georgia Research Foundation, Inc., GA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/347,959

(22) Filed: Jul. 6, 1999

(65) Prior Publication Data

US 2001/0006953 A1 Jul. 5, 2001

Related U.S. Application Data

(60) Provisional application No. 60/091,820, filed on Jul. 6, 1998.

(51) Int. Cl.$^7$ .................. A01N 43/04; A61K 39/00; C12N 15/00; C12N 5/00; C07H 21/02
(52) U.S. Cl. ................... 514/44; 424/184.1; 435/320.1; 435/325; 435/455; 536/23.1
(58) Field of Search ................. 514/2, 44; 536/23.1; 435/320.1, 325; 424/455, 184.1

(56) References Cited

U.S. PATENT DOCUMENTS

| | | | |
|---|---|---|---|
| 5,270,180 A | 12/1993 | Cho et al. | 435/69.4 |
| 5,620,896 A | 4/1997 | Herrmann et al. | 435/320.1 |
| 5,780,448 A | 7/1998 | Davis | 514/44 |

OTHER PUBLICATIONS

Anderson, E.D., et al., "Gene Expression in Rainbow Trout (*Oncorhynchus Mykiss*) Following Interamuscular Injection of DNA", *Molecular Marine Biology and Biotechnology*, 5(2), 105–113, (1996).

Anderson, E.D., et al., "Genetic Immunization of Rainbow Trout (*Oncorhynchus Mykiss*) Against Infectious Hematopoietic Necrosis Virus" *Molecular marine Biology and Biotechnology*, 5(2), 114–122, (1996).

Bourne, N., et al., "DNA Immunization Against Experimental Genital Herpes Simplex Virus Infection", *Journal of Infectious Diseases*, 173(4), 800–807, (1996).

Chimanat, C., et al., "Bacterial Plasmid DNA Induces Non–specific Cytotoxic Cells of Channel Catfish (*Ictalurus Punctatus*) In Vivo", *30th Annual Conference of the International Association for Aquatic Animal Medicine*, Boston, Massachussetts, 41, (May, 1999).

Clark, T.G., et al., "Mechanisms of Immunity Against the Parasitic Ciliate, *Ichthyopthirius Multifiliis*", *23rd annual Eastern Fish Health Workshop Proceedings*, 1 P, (1998).

Daheshia, M., et al., "Suppression of Ongoing Ocular Inflammatory Disease by Topical administration of Plasmid DNA Encoding IL–10", *Journal of Immunology*, 159(4), 1945–1952, (Aug. 1997).

Davison, A.J., et al., "Identification of Structural Proteins of Channel Catfish Virus by Mass Spectrometry", *Virology*, 206(2), 1035–1043, (1995).

Francis, C.H., et al., "Production of Lymphokine (Macrophage Activating Factor) by Salmon (*Salmo Salar*) Leucocytes Stimulated With Outer Membrane Protein Antigens of *Aeromonas Salmonicida*.", *Fish & Shell Immunology*, 4(7), 489–497, (1994).

Fu, T.M., et al, "Protective Cellular Immunity: Cytotoxic T–Lymphocyte Responses Against Dominant and Recessive Epitopes of Influenza Virus Nucleoprotein Induced by DNA Immunization", *Journal of Virology*, 71(4), 2715–2721, (1997).

Fynan, E.F., et al., "DNA Vaccines: Protective Immunization by Parenteral, Mucosal, and Gene–gun Inoculations.", *Proceedings of the National Academy of Sciences of the USA*, 90(24), 11478–11482, (Dec. 1993).

(List continued on next page.)

*Primary Examiner*—Scott D. Priebe
*Assistant Examiner*—Sumesh Kaushal
(74) *Attorney, Agent, or Firm*—Schwegman, Lundberg, Woessner & Kluth, P.A.

(57) ABSTRACT

Disclosed are methods for delivering a preselected polypeptide into an aquatic animal by contacting the aquatic animal with an aqueous medium containing an isolated non-infectious, non-integrating polynucleotide encoding an immunogen, wherein the polynucleotide is operably linked to a promoter that controls the expression of the polynucleotide in the aquatic animal, and wherein expression of the polypeptide stimulates a detectable biological response in the animal. Also disclosed are methods for delivering a desired polynucleotide into an aquatic animal comprising contacting the aquatic animal with an aquatic medium containing an isolated non-infectious, non-integrating polynucleotide, wherein the polynucleotide is substantially complementary to all or a portion of a messenger RNA (mRNA) encoding a preselected polypeptide, and wherein expression of the polypeptide stimulates or represses a detectable biological response in the animal. Methods are further disclosed for delivering a preselected polynucleotide into an aquatic animal comprising contacting the aquatic animal with an aqueous medium containing an isolated non-infectious, non-integrating polynucleotide that is not in contact with a liposome or lipid carrier, wherein the polynucleotide stimulates a detectable biological response in the animal.

27 Claims, No Drawings

OTHER PUBLICATIONS

Gomez–Chiarri, G., et al., "Development of Vaccines Against Bacterial Diseases in Salmonid Fishes Using DNA Immunization", *23rd Annual Eastern Fish Health Workshop Proceedings 23:21*, 1 P., (1998).

Gomez–Chiarri, M., et al., "Introduction of Foreign Genes into Tissue of Live Fish by Direct Injection and Particle Bombardment", *Diseases of Aquatic Organisms*, 27, 5–12 (Oct. 1996).

Hansen, E., et al., "Strong Expression of Foreign Gene Following Direct Injection into Fish Muscle", *Federation of European Biochemical Societies Letters*, 290(1/2), 73–76 (Sep. 1991).

Hirst, I.D., et al., "Iron–regulated Outer Membrane Proteins of *Aeromonas Salmonicida* are Important Protective Antigens in Atlantic Salmon Against Furunculosis.", *Fish & Shell Immunology*, 4(1), 29–45, (1994).

Johnsson, J.I., et al., "Growth Hormone Increases Growth Rate, Appetite and Dominance in Juvenile Rainbow Trout, *Onchorhynchus Mykiss*", *Animal Behaviour*, 48, 177–186, (1994).

Kodihalli, S., et al., "Cross–Protection Among Lethal H4N2 Influenza Viruses Induced by DNA Vaccine to the Hemagglutinin", *Journal of Virology*, 71(5), 3391–3396, (May, 1997).

Rahman, A., et al., "Fish Transgene Expression by Direct injection into Fish Muscle", *Molecular Marine Biology and Biotechnology*, 1(4/5), 286–289, (1992).

Siharath, K., et al., "Regulation of IGF–binding Proteins by Growth Hormone in the Striped Bass, *Morone Saxatilis*", *Molecular Marine Biology and Biotechnology*, 4(2), 171–178, (1995).

Stanley, L.A., et al., "Extracellular Products Associated With Virulent and Avirulent Strains of *Edwardsiella Ictaluri* From Channel Catfish", *Journal of Aquatic Animal Health*, 6(1), 36–43, (1994).

Ulmer, J.B., et al., "Heterologous Protection Against Influenza by Injection of DNA Encoding a Viral Protein", *Science*, 259, 1745–1749, (1993).

Feguson, H. W., "Systemic Pathology of Fish: A Text And Atlas of Comparative Tissues Responses in Diseases of Telecosts", *Iowa State University Press, Ames Iowa*, 2 Pages (1989).

Roberts, R. J., "Fish Pathology", *2nd edition, ed, Roberts R. J. 2 Pages*, (1989).

Ferguson, H.W., "Systemic Pathology of Fish: A Text and Atlas of Comparative Tissue Responses in Diseases of Teleosts", *Iowa State University Press*, Ames Iowa, 2 pp., (1989).

Roberts, R.J., "Fish Pathology", *2nd edition, ed. Roberts, R.J.*, 2 pp., (1989).

Fernandez–Alonso, M. et al. A Model to Study Fish DNA Immersion Vaccination by using the Green Fluorescent Protein, Journal of Fish Diseases 22(3):237–241, May 1999.*

Houdebine, L.M. et al. Transgenesis in Fish. Experientia 47(9):891–897, Sep. 1991.*

Liu, Z. et al. Development of Expression Vectors for Transgenic Fish. Bio/Technology 8:1268–1272, Dec. 1990.*

Anderson, W.F. Human Gene therapy. Nature 392(Supplement):25–30, Apr. 1998.*

Miller, N. et al. Targeted Vectors for Gene Therapy. FASEB Journal 9:190–199, 1995.*

Verma, I.N. Gene Therapy—Promises, Problems and Prospects. Nature 389:239–242, May 1999.*

Anderson et al., Genetic immunization of rainbow trout (*oncorhynchus mykiss*) against infectious hematopoietic necrosis virus, 1996, Molecular Marine Biology and Biotechnology, vol. 5 No. 2, pp. 114–122.*

Gudding et al., Recent developments in fish vaccinology, 1999, Veterinary Immunology and Immunopathology, vol. 72, pp. 203–212.*

* cited by examiner

DELIVERY OF NUCLEIC ACID INTO AQUATIC ANIMALS

RELATED APPLICATION

This application claims the benefit of U.S. Provisional Application Ser. No. 60/091,820, filed Jul. 6, 1998 under 35 USC119(e).

BACKGROUND OF THE INVENTION

Seafood and fishery products are currently very popular in the United States and around the world. Per capita consumption of fishery products in the United States increased 25 percent in the 1980s (Tucker and Robinson, 1990). In 1994, each American ate an average of 15.2 pounds of seafood, of which 54 percent was imported (Harvey, 1996).

Fishery products reach the table of the consumer from three major sources: commercial harvest of wild species, recreational harvest of wild species, and aquaculture. Growing public concern for the decline in commercially important wild fish stocks and steady demand for fishery food items has enabled aquaculture to become a rapidly emerging component of the United States agricultural industry. Compared with terrestrial food animal production industries, very little is known about the health management aspects of cultured aquatic food species, especially with regard to infectious disease.

Viral and bacterial diseases in fin-fish, shellfish or other aquatic lifeforms pose a serious problem for the aquaculture industry. Owing to the high density of animals in the hatchery tanks or enclosed marine farming areas, infectious diseases may eradicate a large proportion of the stock in, for example, a fin-fish, shellfish, or other aquatic lifeforms facility. Prevention of disease is a more desired remedy to these threats to fish than intervention once the disease is in progress. Vaccination of aquatic animals is the only preventative method which may offer long-term protection through immunity.

Vaccination with inactivated or attenuated organisms or their products has been shown to be an effective method for increasing host resistance to infection by various organisms. The use of vaccines is based on the stimulation of specific immune responses within a host or the transfer of preformed antibodies. Effective vaccines have been developed for relatively few of the infectious agents that cause disease in domestic and aquatic animals. This often reflects technical problems associated with the growth and attenuation of virulent strains of pathogens.

The fish immune system has many features similar to the mammalian immune system, such as the presence of B cells, T cells, lymphokines, complement, and immunoglobulins. Fish have lymphocyte subclasses with roles that appear similar in many respects to those of the B and T cells of mammals. Additionally, the efficiency of the immune response of fish can be affected by outside stresses, as is true in mammals. However, fish, unlike mammals, display a temperature-dependent development of protective immunity in response to antigens.

A. Development of DNA Vaccines

Effort recently has been placed on the development of subunit vaccines. A subunit vaccine consists of only limited components, most commonly proteins, of an infectious agent. Subunit vaccines have the potential for achieving high levels of protection in the virtual absence of side effects. Subunit vaccines also offer the opportunity for the development of vaccines that are stable and easy to administer.

A rapidly emerging variation of subunit immunization is genetic vaccination, also called DNA-mediated or plasmid vaccination. Genetic immunization uses naked DNA to immunize the recipient. The DNA is "naked" in the sense that it is free from any infectious delivery vehicle that can act to facilitate entry into the cell, such as viral particles. This approach is based on the finding that skeletal muscle cells injected with naked DNA are able to express the plasmid DNA-encoded proteins. The newly synthesized antigen can then stimulate a specific immune response composed of cytotoxic T cells, T-helper cells, and antibodies. Using such DNA vaccines, there is no longer a need to purify the pathogen or immunoprotective antigen for vaccination and no possibility of reversion to virulence because the DNA encodes a single viral protein.

DNA vaccines also overcome many of the subunit vaccine limitations, such as expensive production costs and poor immunogenicity, because they directly introduce only specific genes encoding protective proteins into the host and use the host cell protein synthesis machinery to produce the antigen in situ. Thus, immunization is accomplished by host cells taking up and expressing an inoculated polynucleotide. Moreover, genes that code for other proteins, such as regulatory molecules or hormones, can also be used to modulate the physiology of the target animal. Such proteins can also provide an anti-tumor response, or provide contraception.

The uptake of the DNA by host cells can result in the expression of a preselected antigen or antigens, thereby eliciting humoral or cell-mediated immune responses or both humoral and cell-mediated responses. The term "immune response" refers to a cytotoxic T cell response or increased serum levels of antibodies to an antigen. The term "immunizing" refers to the production of an immune response in a vertebrate which protects (partially or totally) from the manifestations of infection or disease caused by an infectious agent. That is, a vertebrate immunized with a DNA vaccine will not be infected or will be infected to a lesser extent than would occur without immunization.

The elicited humoral and/or cell-mediated immune response can provide protection or protective immunity against infection by pathogenic agents such as bacteria, viruses and eukaryotic organisms (e.g., parasites). The protective humoral and/or cell-mediated immune responses then interfere with the infectivity or activity of the pathogen, or limit its spread or growth, resulting in protection against subsequent challenge by the pathogen. The immune response may also combat diseases and disorders involving cells that produce specific proteins.

The DNA is expressed by the animal cells and appears to stimulate persistent humoral and/or cellular responses without integration of plasmid into chromosomal DNA. Direct DNA administration obviates the lengthy and costly requirement for purified antigens. Moreover, the resultant prolonged antigen production in vivo approximates the immune system response following immunization with a live, attenuated virus or live recombinant vaccine without the risk of infection or the necessity of adjuvants and boosters.

DNA immunization via intramuscular injection has been shown to be effective in various animals against many viruses. For example, the immunization of guinea pigs against herpes simplex virus (HSV) type 2 infection (Bourne et al. (1996)); the immunization of mice against influenza virus (Fu et al. (1997)); the vaccination of chickens against influenza viruses (Kodihalli et al. (1997)); and mammals and avians against rotaviruses (Herrmann et al. U.S. Pat. No. 5,620,896). Daheshia et al. (1997) disclose that a single application of naked DNA encoding IL-1 0 to the cornea of animals expressing herpetic stromal keratitis resolved the lesions affecting these animals, causing lesion remission.

Thus, DNA vaccination provides a novel method to induce both humoral and/or cell-mediated immunities. The simplicity of the technology, and its ability to induce antibody (Ab) and cytotoxic T-lymphocyte (CTL) responses in animals with different genetic backgrounds, and its preclinical efficacy in a variety of disease models suggest that DNA vaccination is a useful approach for vaccine development. Additionally, the ability of DNA vaccines to induce immune responses with non-replicating material offers an alternative to live vectors or pathogens for eliciting cell-mediated immunity for those instances where such agents may present potential safety concerns. Also, because the immune response that is generated is broad based, the immune response elicited by DNA vaccination is particularly effective to protect against pathogen infection or combat cells associated with hyperproliferative diseases or autoimmune diseases.

B. Direct DNA Immunization/Transfection Administered by Injection or Particle Bombardment In the past, methods of transferring genes into live animals in vivo required either viral vectors and/or liposome carriers containing DNA, or a receptor-mediated soluble DNA carrier system. Animals used were either fetal or newborn mice and rats, and expression was mostly found in liver and spleen. Later, direct gene injection of naked DNA or RNA into mouse skeletal muscle and into rat myocardium in vivo was performed. Other researchers found high levels of expression following direct injection of foreign genes into fish skeletal muscle. The histochemical analysis revealed that the constructs were expressed in distinct muscle cells in the injection area.

Direct injection of DNA into the somatic tissues of animals is a powerful strategy for immunization and gene therapy. The technique also provides an attractive alternative to the creation of transgenic animals that have the transgene stably incorporated into the genome. Not only is direct injection technologically simple, as it can be carried out with a hypodermic needle and syringe, but the biological effect of the gene transfer is relatively immediate. Expression of transgenes such as the cytokines interleukin 2 and 4, and transforming growth factor-β1, human dystrophin, the NP gene of influenza, and the reporter genes β-galactosidase, firefly luciferase, and chloramphenicol acetyl transferase (CAT) has been demonstrated in animals after direct DNA injection. The technique bypasses the time-consuming selection of transgene germline carriers over several generations and its potential for effecting measurable phenotypic changes in farmed animals being examined.

In fish, biologically active foreign DNA has been delivered by electroporation and microinjection of developing embryos and sperm. Studies have demonstrated that both mammalian and fish promoters are effective in promoting the expression of foreign DNA in fish. Furthermore, the tissue specificity of expression in fish by these promoters is often similar to that observed in mammalian species. Direct injection of DNA in the muscle of tilapia fish (*Oreochromis niloticus*) has resulted in the expression of the reporter gene CAT, driven by the carp β-actin promoter. These results indicate that transient transcription; following direct in vivo injections of a transgene into skeletal muscle, as previously measured in both mouse and rat can also be detected in fish muscle.

C. Vaccines for Aquatic Animals Administered by Injection

The introduction of novel cloned DNA sequences into fish has now become a common procedure and has an important bearing on aquaculture. To introduce recombinant DNA in fish, it is necessary to use gene constructs comprising a promoter that will drive expression of the linked protein coding sequence in the chosen fish species. Reporter genes that can be detected by simple assay procedures are routinely used to identify transformed cells. In most procedures, determination of satisfactory expression in tissues of the grown fish involves introduction of the DNA sequences into fertilized eggs by microinjection or electroporation, followed by waiting for a period of weeks or months until fish have grown to a size at which adult organs can be sampled for expression of the transgene. This delay is often necessary because expression in the embryo or fry may be problematical. A quick method of assaying for satisfactory gene promotion has recently been developed in mammals, where copies of the novel gene construct were injected directly into the muscle tissue of adult mice or rats, followed by assays on biopsy samples recovered from the site of injection. It appears that because of the special features of the muscle filament, copies find their way into intact nuclei of damaged fiber cells, and subsequent cell repair allows transient transcription of some gene copies.

It has been shown that rainbow trout will express firefly luciferase and β-galactosidase from naked DNA injected into skeletal muscle. It has been demonstrated that DNA containing infectious hematopoietic necrosis virus (IHNV) glycoprotein (G) gene down-stream of the cytomegalovirus immediate early promoter (CMV-IEP) will induce an immune response in fish. Fish injected with plasmid DNA encoding the IHNV-G protein, or with a combination of plasmid DNAs encoding G protein and nucleoprotein (N) protein, produced a strong protective immune response to subsequent challenge with a lethal dose of IHNV. Expression of injected or particle bombarded reporter genes under the control of mammalian promoter sequences has been demonstrated in the common carp (*Cyprinus carpio*), tilapia (*Oreochromis niloticus*), and rainbow trout (*Oncorhynchus mykiss*) (Hansen et al., 1991; Rahman and Maclean, 1992; Anderson et al., 1996a; Gomez-Chiarri et al., 1996).

Research has demonstrated that genetic vaccination has elicited protective immunity in a number of different animal models, including rainbow trout (Fu et al., 1997; Kodihalli et al., 1997; Bourne et al., 1996; Anderson et al., 1996b). In some cases the protection provided by the genetic vaccine was more effective than conventional whole-virus vaccine (Kodihalli et al., 1997). While the most common route of administration of plasmid DNA is by intramuscular injection or intradermal injection, in mammals and birds mucosal absorption has also been successful (Fynan et al., 1993b). Mucosal delivery has not been shown to be effective in fish.

Few antiviral vaccines have been marketed for fish. This is largely due to the difficulty of growing virus in culture for the production of whole killed viral vaccines or safe attenuated strains of virus. Antigen-based vaccines using purified recombinant proteins are difficult and expensive to produce in large scale and may have poor immunogenicity in fish.

As with most commercially important food animals, there is a need for novel systems to vaccinate fin-fish, shellfish, and other aquatic animals against diseases. These systems should be inexpensive to produce and administer, avoid the use of live, attenuated organisms, and induce strong and long-lasting immunity preferably without boost and with induction of both antibodies and cell-mediated immunity. More preferably, the system should be applicable to very small cultured aquatic animals, be less stressful to the animals during administration, and have the capacity of simultaneously immunizing large numbers of animals for reduced labor-related costs.

SUMMARY OF THE INVENTION

The present invention relates to a method for delivering a preselected polypeptide into an aquatic animal by contacting the aquatic animal with an aqueous medium containing an isolated non-infectious, non-integrating polynucleotide that is not in contact with a liposome or lipid carrier, wherein the polypeptide is operably linked to a promoter that controls the expression of the polynucleotide in the aquatic animal, and wherein expression of the polypeptide stimulates a detectable biological response in the animal.

The present invention also provides a method for delivering a preselected polynucleotide into an aquatic animal by contacting the aquatic animal with an aqueous medium containing an isolated non-infectious, non-integrating polynucleotide that is not in contact with a liposome or lipid carrier, wherein the polynucleotide stimulates a detectable biological response in the animal.

The present invention further provides a method for inducing an immune response in an aquatic animal, comprising contacting the aquatic animal in an aqueous medium containing an isolated noninfectious polynucleotide, wherein the polynucleotide is present in a sufficient amount so that cellular uptake of the polynucleotide occurs so as to induce the immune response, and wherein the polynucleotide is not in contact with a liposome or lipid carrier.

The contacting step is preferably carried out by immersing the aquatic animal, such as a fish, either partially or fully in a solution comprising the polynucleotide. The contacting step may alternatively be performed by spraying the medium onto the animal. The medium may contain a non-lipid or liposome uptake enhancing material to facilitate entry of the polynucleotide into the cell. The medium may contain salts or nutrients for the animal.

The polynucleotide may be DNA. It may be plasmid DNA. The promoter may be a cell-specific or tissue specific promoter. Further, the DNA may be operably linked to a DNA sequence encoding a signal peptide wherein the signal peptide directs the secretion of the polypeptide in preselected cells.

The polynucleotide may be translated for a limited period of time so that the polypeptide expression is transitory. The polypeptide can be produced in vivo for at least one month, or for at least 10 days, or for less than 10 days. The polypeptide may be expressed in a therapeutic amount. The polypeptide may comprise an enzyme, a hormone, an immunomodulator, a lymphokine, a substance that manipulates reproduction, a growth promoting or growth inhibiting substance, or a substance that controls abnormal cell growth. Further, it may be an immunogen.

An advantage of prolonged synthesis of antigen is the induction of an immune response as soon as the immune system is mature. Fish may be unable to induce sufficient immune responses at a young age. For example, trout and halibut may not produce lymphoid cells until as late as ten and thirty days after hatching, respectively, and T-dependent immune responses do not appear until months after hatching. Using the methods of this invention, expression of foreign protein in fish can continue at least four months after transfection indicating that genetic immunization may be preferred for vaccination of young fish.

Aquaculture species treated by methods of this invention include a diversity of species of cultured fin-fish, shellfish, and other aquatic animals. Fin-fish include all vertebrate fish, which may be bony or cartilaginous fish. A preferred embodiment of this invention is the immunization of fin-fish. These fin-fish-include but are not limited to salmonids, carp, catfish, yellowtail, seabream, and seabass. Salmonids are a family of fin-fish which include trout (including rainbow trout), salmon, and Arctic char. Examples of shellfish include, but are not limited to, clams, lobster, shrimp, crab, and oysters. Other cultured aquatic animals include, but are not limited to eels, squid, and octopi. The polypeptide can be administered to commercially important aquatic animals such as channel catfish, salmonids, tilapia, hybrid striped bass, arctic char, carp, sturgeon, flounder, koi, angel fish, gourami, eel or crustaceans, such as shrimp, prawns, lobsters or crabs.

The present invention also provides a method for inducing an immune response in an aquatic animal, where the aquatic animal is contacted with an aqueous medium containing an isolated noninfectious polynucleotide linked to a promoter that can control the expression of the polynucleotide in the aquatic animal. The polynucleotide encodes an immunogenic polypeptide. The amount of polynucleotide is sufficient so that uptake of the polynucleotide occurs, and expression results, so as to induce an immune response in the animal. The immune response may be protective.

In this method, the polynucleotide is free from a protein coat delivery vehicle, such as a virion. The immunogen may be a viral protein or peptide, a parasite antigen, a fungal antigen, or a bacterial virulence factor, such as an inactive protein toxin or a fragment of a bacterial toxin. The polynucleotide is also free of liposomes or other lipid carriers. In other words, the aquatic animal need not be immersed in a solution of liposome formulated DNA in order for the vaccine to be effective. The medium in which the animal is immersed may contain an effective amount of an immunological adjuvant.

Also provided is a method for delivering a preselected polynucleotide into cells of an aquatic animal, comprising contacting the aquatic animal with an aqueous medium containing an isolated non-infectious, non-integrating polynucleotide encoding the polypeptide, wherein the polynucleotide is substantially complementary to all or a portion of a messenger RNA (mRNA) encoding a preselected polypeptide, and wherein the expression of the polypeptide stimulates or represses a detectable biological response in the animal. In other words, in this method, the polynucleotide may be an "antisense" polynucleotide.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the preferred methods and materials are described below. All publications, patent applications, patents, and other references mentioned herein are incorporated by reference. In addition, the materials, methods, and examples are illustrative only and not intended to be limiting.

Other features and advantages of the invention will be apparent from the detailed description, and from the claims.

DETAILED DESCRIPTION OF THE INVENTION

A. Definitions

The term "polypeptide" is understood to be any translation product of a polynucleotide regardless of size, and whether glycosylated or not. Further, the term "polypeptide" may be used interchangeably with the terms "protein" or "peptide". Preferably, the polypeptides of the invention are biologically active. For example, a "biologically active"

polypeptide, subunit, or variant thereof of the invention has at least about 1%, preferably at least about 10%, more preferably at least about 50%, and even more preferably at least about 90% of the activity of a chosen polypeptide. The activity of polypeptide of the invention can be measured by methods well known to the art including, but not limited to, the ability of the polypeptide to be bound by antibodies specific for the target polypeptide, the ability of the polypeptide to elicit a sequence-specific immunologic response when the polypeptide is administered to an animal.

An isolated "variant" molecule of the invention is a nucleic acid molecule or polypeptide that has at least 80%, preferably at least about 90%, and more preferably at least about 95%, but less than 100%, contiguous sequence homology or identity to the nucleotide or amino acid sequence of the corresponding wild type nucleic acid molecule or polypeptide. Moreover, a variant nucleic acid molecule or polypeptide of the invention may include nucleotide bases or amino acid residues not present in the corresponding wild type nucleic acid molecule or polypeptide, as well as internal deletions relative to the corresponding wild type molecule.

Polypeptides or variants thereof which are subjected to chemical modifications, such as esterification, amidation, reduction, protection and the like, are referred to as "derivatives." For example, a modification known to improve the immunogenicity, stability and/or bioavailability of peptides in vivo is the cyclization of the peptide, for example through one or more disulfide bonds.

A "biologically active" polypeptide may be an antigen derived from an infectious agent, or an antigenic fragment or polypeptide that has been experimentally determined to be immunogenic, and is preferably effective in immunizing a target animal against infection by the pathogenic agent. The preselected antigen to be expressed is designed so as to give internal, surface, secreted, or budding and assembled forms of the antigens being used as immunogens. The polynucleotide may, alternatively encode a peptide that has contraceptive or anti-cancer properties.

An "immunostimulant" is an agent that stimulates the immune response. Such a molecule can stimulate any aspect of the immune response, either an innate or an adaptive immune response.

A "preselected antigen" can be any antigen expressed by an infectious agent or any antigen that has been determined to be capable of eliciting an immune response, preferably a protective response against an infectious agent. These antigens may or may not be structural components of the infectious agent. The encoded antigens can be translation products or polypeptides. The polypeptides can be of various lengths. They can undergo normal host cell modifications such as glycosylation, myristoylation or phosphorylation. In addition, they can be designed to undergo intracellular, extracellular or cell-surface expression. Furthermore, they can be designed to undergo assembly and release from cells.

As used herein, the term "purified" refers to in vitro preparation and purification of an isolated nucleic acid molecule, polypeptide or peptide of the invention, so that it is not associated with in vivo substances and is substantially free of infectious agents.

The term "isolated" nucleic acid means DNA or RNA that is free of the genes and other nucleotide sequences that flank the gene in the naturally occurring genome of the organism from which the isolated DNA or RNA of the invention is derived. The term therefore includes, for example, a recombinant DNA which is incorporated into a vector, into an autonomously replicating plasmid or into the genomic DNA of a prokaryote or eukaryote, or which exists as a separate molecule (e.g., a cDNA or a genomic or cDNA fragment produced by PCR or restriction endonuclease digestion) independent of other sequences. It also includes a recombinant DNA which is part of a hybrid gene encoding additional polypeptide sequences. "Polymerase chain reaction" or "PCR" refers to a procedure or technique in which amounts of a preselected fragment of nucleic acid, RNA, and/or DNA, are amplified as described in U.S. Pat. No. 4,683,195.

B. Immersion Delivery of Nucleic Acid into an Aquatic Animal

Genetic immunization has several advantages. The antigenic protein is synthesized in vivo giving rise to both humoral and cell-mediated (cytotoxic T lymphocytes) immune responses. However, unlike live attenuated pathogens, which also synthesize protein in vivo, DNA vaccines carry no risk of inadvertent infection. Unlike antigen-based immunization, genetic vaccination does not require the use of traditional adjuvants to generate an effective immune response. Furthermore, DNA used in the methods of this invention is inexpensive and is easy to manufacture and purify.

Genetic immunization also allows the host animal to produce foreign antigens within its own tissue thereby resulting in several advantages. One advantage is the efficient presentation of the foreign antigen to the immune system due to the expression of a protein within a self-cell, which could be an antigen-presenting cell. Another advantage is the correct folding, protein modification, and disulfide bonding of a protein expressed in a host cell, especially for viral proteins, which are normally produced in cells of hosts. Recombinant viral proteins synthesized in bacterial or yeast cells may be incorrectly post-translationally modified and are often massed in inclusion bodies, which make the proteins difficult to purify or ineffective if administered in unpurified form.

Immune responses in fish are temperature dependent. Antigen-based vaccines may give rise to sub-optimal immune responses if such vaccines are given at the wrong temperature. Genetic immunization is advantageous because expression of the antigenic protein could continue over a long period until such time as to stimulate an immune response when the temperature is optimal.

The present invention describes a new process by which aquatic animals can be vaccinated by exposure to a solution comprising nucleic acid molecules. To practice the present invention, a naked polynucleotide is prepared which operatively codes for a preselected biologically active polypeptide for incorporation into aquatic animal cells. The polynucleotide is then administered to the animal by immersing the animal in a medium containing the polynucleotide. The polynucleotide may enter cells of the epithelium of the skin, the gills or the gut wall. The polynucleotide may then be expressed in these transfected cells leading to induction of appropriate immune responses in regional or systemic lymphoid tissue. Alternatively, the polynucleotide itself may induce the biological response. For example, it may be an immunostimulant.

The immersion route of delivery is unique for aquatic animal species because of the liquid aqueous environment. The nucleic acid molecules of the present invention directly transfect the cells of fish, or other aquatic animals, and are capable of expressing an infectious disease protective antigen, immunomodulating protein, reproductive hormone, or growth hormone. It is believed that this process will have great utility in the growing aquaculture industry.

Prior research in DNA immunization with aquatic animals only used injection and particle bombardment as modes of administration because of the perception that the DNA molecules that comprise the vaccine will be degraded in the immersion bath before adequate DNA uptake is achieved by the aquatic animal. This logic is expressed by Gomez-Chiarri and co-workers (1996) in their discussion of particle bombardment is a more effective means of DNA delivery, in trout, than intramuscular injection, in which they state that much of the DNA following an intramuscular injection is degraded in the intracellular space before it is taken up by the muscle cells.

It was previously thought that muscle cells were unique among cell types in their capacity to take up and express free DNA, although one group of researchers were able to effectively immunize mice against the influenza virus by using particle bombardment of the epidermis (Fynan et al. 1993). Further, when other researchers attempted to inject DNA into the gills and the peritoneum of trout, no expression was observed in tissue lysates from these fish when they were sacrificed two days after injection. Thus, it was not expected that foreign DNA would be taken up by gill tissue and expressed.

Moreover, previous patents granted for genetic vaccines in mammals do not disclose or suggest the immersion route of DNA delivery, but only disclose parenteral and topical delivery methods. Therefore, the effectiveness of this DNA delivery process was unexpected and provides significant utility in vaccinating large numbers of often very small cultured aquatic animals.

A variety of infectious disease agents are currently a problem in the aquaculture industry. By identifying protective antigens associated with these various agents, immersion genetic vaccination will help improve production yields in aquaculture facilities. Methods of this invention may be useful in the immunization of aquaculture species against various pathogens, such as viruses, bacteria, parasites or fungi. For example, the group of pathogens includes but is not limited to hemorrhagic septicemia virus, infectious hematopoietic necrosis virus, infectious pancreatic necrosis virus, virus causing spring viremia of carp, channel catfish virus (*Herpesvirus ictaluri*), grass carp hemorrhagic virus, nodaviridae such as nervous necrosis virus or striped jack nervous necrosis virus, infectious salmon anaemia virus, *Aeromonis salmonicida, Renibacterium salmoninarum*, Yersinia, Pasteurella (including piscicida), Vibrosis (including anguillarum and ordalii), Edwardsiella (including ictaluri and tarda), Streptococci, and Ichthyophthirius.

Channel catfish culture is one of the largest aquatic agriculture industries in the United States. Two examples of infectious disease agents that may be controlled by genetic immunization are channel catfish virus (CCV) and the bacterium *Edwardsiella ictaluri*. Strong catfish cellular immune responses are required for adequate protection against both of these agents and immunization with CCV envelope glycoproteins (Davison and Davison, 1995) *E. ictaluri* chondroitinase-like enzymes (Stanley, et al., 1994), or other pathogen gene products may provide disease protection. Additionally, protozoan parasite disease, such as *Ichthyopthirium multifiliis*, may be controlled by this invention.

The salmonid culture industry is also threatened by a variety of viral and bacterial infectious agents. Infectious hematopoietic necrosis virus, infectious pancreatic necrosis virus, onchorhynchus masou virus, viral hemorrhagic septicemia, and herpesvirus salmonis, and infectious salmon anemia virus are viral agents that cause high mortality in susceptible fish (Heppell, et al., 1995; Bouchard et al., 1998). Bacterial pathogens responsible for high morbidity and mortality in salmonid aquaculture include *Aeromonas salmonicida, Vibrio anguillarum, Yersinia ruckerii*, and *Renibacterium salmoninarum* (Stoskopf, 1993; Hirst and Ellis, 1994).

Other food fish species are currently used in culture operations around the world. Some examples of these fish include: tilapia, hybrid striped bass, arctic char, carp, eel, and various other species. While disease agents for less well-known aquaculture species are less well understood, the present invention can deliver immunogenic proteins, preferably for preventative genetic-based therapeutics.

As more species of ornamental fish are grown in captivity, infectious diseases associated with their culture will become more of a problem. Examples of these agents include *Flavobacterium columnare*, herpesvirus carpio, spring viremia of carp virus, cichlid iridovirus, lymphocystis, and various protozoan parasites (Stoskopf, 1993).

Infectious disease is one of the biggest problems in the shrimp culture industry. White spot virus, taura syndrome, and yellowhead virus are examples of important viral agents in shrimp aquaculture. The pathogen *Vibrio parahaemolyticus* is an example of a bacterial agent that causes disease in culture shrimp (Mikulski et al., 1998). Unfortunately, shrimp do not have a memory component to their immune system. Vaccination in the true sense of the term is not possible for invertebrates, but innate immunity may be enhanced with the use of specific pathogen antigens. These antigens, delivered by this invention may enhance the shrimp defense mechanisms and enable better yields for the producer.

Enhancing defense mechanisms in aquatic animals may also be accomplished by immersion DNA vaccination. Cytokines that modulate the immune response in aquatic organisms have been identified (Francis and Ellis, 1994; Tamai et al., 1993; Daheshia et al., 1997). By constructing plasmids that express these immunomodulators, and administering them alone or in combination with specific antigen plasmid constructs, immunity in aquatic animals may be enhanced (Francis and Ellis, 1994). Immunomodulation, therefore, may help innate defenses in organisms, such as shrimp, that lack a specific, memory-driven immune system. Moreover, growth-enhancing proteins may be delivered to the organisms by immersion DNA vaccination. These gene products will increase the growth efficiency of cultured aquatic food animals (Cho et al., 1993; Johnsson and Bjoemsson, 1994; Siharath et al. 1995).

The polynucleotide that encodes an immunogenic peptide, polypeptide or protein is directly administered to an animal in vivo. The polynucleotide encodes a polypeptide that shares at least one epitope with an immunogenic protein to be targeted. The polynucleotide is expressed by the individual's cells to form immunogenic target proteins that elicit an immune response that is broad based.

There are numerous advantages for the use of polynucleotides for immunizations. For example, immunization can be accomplished using any antigen encoded by a polynucleotide. Furthermore, the polynucleotide encoded antigens are expressed as "pure" antigens in their native states and have undergone normal host cell modifications. Also, polynucleotides are easily and inexpensively manipulated and are stable as a dry product or in solution over a wide range of temperatures. Thus, this technology is valuable for the development of highly effective subunit vaccines.

The naked polynucleotide materials used according to the methods of the invention comprise DNA sequences or DNA sequences coding for polypeptides that have useful therapeutic applications. These polynucleotide sequences are naked in the sense that they are free from any infectious delivery vehicle that can act to facilitate entry into the cell. For example, the polynucleotide sequences are free of virions, which are infectious viral particles.

The DNA sequences may be used in conjunction with an uptake enhancing material, i.e., a non-infectious material that promotes transfection, such as transfection-facilitating proteins, or precipitating agents such as $CaPO_4$.

The DNA sequences used in these methods can be those sequences which do not integrate into the genome of the host cell. These may be non-replicating DNA sequences, or specific replicating sequences genetically engineered to lack the genome-integration ability.

The polynucleotide sequences of the invention are DNA or RNA sequences having a biological, preferably a therapeutic, effect after being taken up by a cell. Examples of polynucleotides that are themselves therapeutic are antisense DNA and RNA or DNA coding for tRNA or rRNA to replace defective or deficient endogenous molecules. The polynucleotide of the invention can also code for therapeutic polypeptides. Therapeutic polypeptides include as a primary example, those polypeptides that can compensate for defective or deficient species in an animal, or those that act through toxic effects to limit or remove harmful cells from the body.

Polynucleotide sequences of the invention preferably code for therapeutic or immunogenic polypeptides, and these sequences may be used in association with other polynucleotide sequences coding for regulatory proteins that control the expression of these polypeptides. The regulatory protein can act by binding to genomic DNA so as to regulate its transcription; alternatively, it can act by binding to messenger RNA to increase or decrease its stability or translation efficiency.

By the term "operably linked to transcriptional and translational regulatory sequences" is meant that a polypeptide coding sequence and minimal transcriptional and translational controlling sequences are connected in such a way as to permit polypeptide expression when the appropriate molecules (e.g., transcriptional activator proteins) are bound to the regulatory sequence(s). In the present invention, polypeptide expression in a target aquatic animal cell is particularly preferred.

The polynucleotide material delivered to the cells in vivo can take any number of forms, and the present invention is not limited to any particular polynucleotide coding for any particular polypeptide. Plasmids containing genes coding for a large number of physiologically active peptides and antigens or immunogen have been reported in the literature and can be readily obtained by those of skill in the art.

The polynucleotide can encode one or multiple antigens, such as antigens from two or more different viral proteins. Alternatively, the polynucleotide may contain one or more different DNA sequences, one sequence encoding an antigen and the others encoding polypeptides which may or may not be antigenic. For example, the vector may encode two antigens from the same pathogen. Alternatively, the different antigen(s) may induce an immune response against a different pathogen and thus serve as a multivalent vaccine. In another embodiment, the other polypeptides may serve to enhance an immune response against a targeted pathogen (e.g., helper epitopes, cytokines, carrier polypeptides, cholera toxin subunits, or other immunostimulants).

The polynucleotide can additionally be inserted into a vector that includes sequences for expression of the polynucleotide. When two or more polypeptide encoding DNA sequences are present in one vector, the transcription of each antigen-encoding DNA sequence may be directed from its own promoter for expression of two or more non-fused polypeptides. Alternatively, one promoter may drive the expression of two or more antigen-encoding DNA sequences joined in frame to each other to express a fusion protein. For example, VP2 and VP3 proteins of infectious pancreatic necrosis virus (IPNV) may be fused. In another embodiment, DNA sequences encoding two or more antigens from different diseases may be joined to form a multivalent vaccine when expressed.

Alternatively, a DNA sequence encoding an antigenic polypeptide may be fused to a DNA sequence encoding a carrier polypeptide. In a preferred embodiment, the carrier polypeptide may contain one or more envelope proteins of the hepatitis B virus, preferably from the human hepatitis B virus. In a more preferred embodiment, the envelope proteins of hepatitis B virus will be the small and major protein (also referred to as surface antigen).

Alternatively, the DNA sequences encoding additional antigens may be administered by using a second vector containing such sequences. Such sequences may encode antigens from the same pathogen or different pathogens, or cytokines, cholera toxin subunits, or other immunostimulants. Such a vector may be administered concurrently or sequentially with the first expression vector. One vector may be induced to express protein simultaneously with or after expression of protein from the other vector.

In yet another embodiment of this invention, antigen-expressing vectors may be administered concurrently with an aptigen-based vaccine such as a recombinant protein or whole-killed vaccine. In a preferred embodiment, the antigen-expressing vector is administered simultaneously with a protein antigen (i.e., recombinant protein or whole killed pathogen). Another preferred embodiment would be to first administer a DNA vaccine to prime the immune response followed by administration of the protein antigen two to eight weeks later, preferably orally or by immersion, to boost the immune response.

The polynucleotide can be administered to an animal in the presence of adjuvants or other substances that have the capability of promoting nucleic acid uptake or recruiting immune system cells to the site of the inoculation. It should be understood that the polynucleotide itself is expressed in the host cell by transcription factors provided by the host cell, or provided by a DNA transcription unit.

According to the methods of the invention, both expressible DNA and mRNA can be delivered to cells to form a polypeptide translation product therein. If the nucleic acids contain the proper control sequences, they will direct the synthesis of relatively large amounts of the encoded protein. When the DNA and mRNA delivered to the cells codes for an immunizing peptide, the methods can be applied to achieve improved and more effective immunity against infectious agents, including intracellular viruses, and also against tumor cells.

One particularly attractive aspect of the invention is a method for obtaining long term administration of a polypeptide to an animal, comprising the step of introducing a naked DNA sequence operatively coding for the polypeptide interstitially into tissue of the animal, whereby cells of the tissue produce the polypeptide for at least one month or at least 3 months, or even at least 6 months.

Another method according to the invention is a method for obtaining transitory expression of a polypeptide into an animal, comprising the step of introducing a naked mRNA sequence operatively coding for the polypeptide interstitially into tissue of the animal, whereby cells of the tissue produce the polypeptide for less than about 20 days, usually less than about 10, days, and even less than 3 or 5 days.

The tissue into which the polynucleotide is introduced can be a persistent, non-dividing cell. The polynucleotide may be either a DNA or RNA sequence. When the polynucleotide is DNA, it can also be a DNA sequence which is itself non-replicating, but is inserted into a plasmid, and the plasmid further comprises a replicator. The DNA may be a sequence engineered so as not to integrate into the host cell genome. The polynucleotide sequences may code for a polypeptide which is either contained within the cells or secreted therefrom, or may comprise a sequence which directs the secretion of the peptide.

The dosage of the immunogenic polypeptide can be readily determined by a clinician or veterinarian employing animal models or other test systems that are well known to the art. Formulations will contain an effective amount of the DNA in an aqueous solution. The amount of DNA to be administered depends upon factors such as the age, weight and physical condition of the animal considered for vaccination. The amount of DNA also depends upon the capacity of the animal's immune system to synthesize antibodies, and the degree of protection desired. Effective dosages can be readily established by one of ordinary skill in the art through routine trials establishing dose response curves. The subject is immunized by administration of the DNA in one or more times. Multiple administrations may be required to maintain a state of immunity by the animal to a particular pathogen.

Such DNA vaccines are stable, easy to administer, and sufficiently cost effective for widespread distribution. Administration of the DNA vaccines of the invention provide in the aquatic animal an immune response or protective immunity to disease caused by the infection.

C. Polynucleotides Delivered into Aquatic Animals

The polynucleotides used for transforming an aquatic animal may be circular or linear, double-stranded of single-stranded. Generally, the polynucleotide is DNA in the form of a plasmid and contains coding regions of beneficial DNA with flanking regulatory sequences which serve to promote the expression of the protein in the aquatic animal. "Heterologous polynucleotides" is used herein to include all synthetically engineered or biologically derived polynucleotides that are introduced into an aquatic animal by a human by genetic engineering, including but not limited to, non-animal genes, modified genes, synthetic genes, portions of genes, as well as polynucleotides from fish and other aquatic animals.

The compositions of and method for constructing heterologous polynucleotides for successful transformations of animals is well know to those skilled in the art, and the same compositions and methods of construction may be used to produce the polynucleotides useful herein. The specific composition of the polynucleotide is not central to the present invention and the invention is not dependent upon the composition of the specific transforming polynucleotide used. Suitable components of the polynucleotide including promoters, polyadenylation sequences, termination signals, splicing signals, selectable markers, reporter genes, enhancers, viral replicons, introns, and bacterial plasmid sequences are well known in the art. Sambrook et al. (1989) provides suitable methods of heterologous polynucleotide construction.

Polynucleotides can be produced by a number of known methods. For example, DNA encoding a preselected antigen can be inserted into an expression vector (see, for example, Sambrook et al. (1989)). With the availability of automated nucleic acid synthesis equipment, DNA can be synthesized directly when the nucleotide sequence is known, or by a combination of PCR, cloning, and fermentation. Moreover, when the sequence of the preselected polypeptide is known, a suitable coding sequence for the polynucleotide can be inferred.

When the polynucleotide is mRNA, it can be readily prepared from the corresponding DNA in vitro. For example, conventional techniques use phage RNA polymerases SP6, T3, or T7 to prepare mRNA from DNA templates in the presence of the individual ribonucleoside triphosphates. An appropriate phage promoter, such as a T7 origin of replication site is placed in the template DNA immediately upstream of the gene to be transcribed. Systems using T7 in this manner are well known, and are described in the literature.

Generally the polynucleotides will be relatively small, i.e., less than about 30 kb to minimize any susceptibility to physical, chemical or enzymatic degradation which is known to increase as the size of the polynucleotide increases.

Suitable polynucleotides for use herein includes all polynucleotides which may provide for, or enhance, a beneficial feature of the aquatic animal. For example, the polynucleotides may encode proteins or antisense RNA transcripts in order to promote increased food values or disease resistance.

The polynucleotides to be introduced into the aquatic animal further will generally contain either a selectable marker of a reporter gene or both to facilitate identification and selection of transformed animals. Alternatively, the selectable marker may be carried on a separate piece of DNA and used in a co-transformation procedure. Both selectable markers and reporter genes may be flanked with appropriate regulatory sequences to enable expression in aquatic animals. Reporter genes which encode for easily assayable marker proteins are well known in the art. In general, a reporter gene is a gene which is not present or expressed the recipient organism or tissue and which encodes a protein whose expression is manifested by some easily detectable property, e.g., phenotypic change or enzymatic activity. Examples of such genes include the chloramphenicol acetyl transferase gene from Tn9 of *E. coli*, and the luciferase genes form firefly *Photinus pyralis*.

Where the polynucleotide is DNA, promoters suitable for use in various animal systems are well known. Promoters useful herein include any constitutive, inducible, tissue or organ specific, or developmental stage specific promoter which can be expressed in the particular aquatic animal. Suitable promoters are described in the prior art. In one embodiment, the DNA sequence includes a cell-specific promoter that permits substantial transcription of the DNA only in predetermined cells. The DNA may also code for a polymerase for transcribing the DNA, and may comprise recognition sites for the polymerase.

A polynucleotide operatively codes for a polypeptide when it has all the genetic information necessary for expression by a target cell, such as promoters and the like. The terms "promoter" or "promoter sequence" herein refers to a minimal sequence sufficient to direct transcription. A DNA polynucleotide sequence is commonly bounded by an initiation site and a termination site to form a DNA transcription unit, and is transcribed to produce a primary transcript.

Other elements such as introns, enhancers, polyadenylation sequences and the like, may also be present on the DNA. Such elements may or may not be necessary for the function of the DNA, although they can provide a better expression of functioning of the DNA by affecting transcription, stability of the mRNA, or the like. Such elements may be included in the DNA as desired to obtain the optimal performance of the transforming DNA in the aquatic organisms. Also included in the invention is an enhancer sequence which may or may not be contiguous with the promoter sequence. Enhancer sequences influence promoter-dependent gene expression and may be located in the 5' or 3' regions of the native gene. Expression is constitutive or inducible by external signals or agents. Optionally, expression is cell-type specific, tissue-specific, or species specific.

To determine whether a particular combination of DNA and recipient aquatic organism are suitable for use herein, the DNA may include a reporter gene. An Assay for expression of the reporter gene may then be performed at a suitable time after the DNA has been introduced into the recipient organism.

D. Polynucleotide Delivery Process

Using the method of the present invention, the target aquatic animal is contacted with a medium containing an isolated non-infectious, non-integrating polynucleotide encoding the polypeptide. The contacting step may be performed by spraying the medium containing the polynucleotide onto the organism one or more times. Alternatively, the contacting step may be carried out by either partially or fully immersing the aquatic animal in the medium containing the polynucleotide. For example, only the head portion of the organism including the gills may be immersed into the medium. The organism may be immersed in the medium briefly, for example for about 1 to 30 seconds, or for a longer period of time, for example for about 1 to 60 minutes, preferably for about 30 minutes. The organism may alternatively be immersed in the medium for about 3 hours to several weeks.

The medium is an aqueous solution containing the polynucleotide. The medium can also contain a non-lipid or liposome uptake enhancing material and/or nutrients and salts suitable for the target organism.

The following example is intended to illustrate but not limit the invention.

EXAMPLE 1

Transfection of Aquatic Animals

The commercially available plasmid pCI (Promega Inc.), an expression plasmid without the gene for β-galactosidase, and pCMV-β (Clontech Inc.), an expression plasmid containing the gene for β-galactosidase, were made in the following manner. The plasmids were purified from *E. coli* strain JM109 cultures by endotoxin-free ion exchange chromatography, according to established protocols (Qiagen Inc.). Ten channel catfish (approximately 15 g each) were immersed, with aeration, in 200 ml of water containing 500 µg of the plasmid pCI or in 200 ml of water containing 500 µg of the plasmid pCMV-β for 30 minutes. After 48 hours, all fish were humanely killed and incubated in an X-gal developing solution for 24 hours before histopathological processing. Tissue sections were then taken of the gills and olfactory organs. β-galactosidase enzyme activity converts X-gal to a dark blue color. Only dark blue staining was observed in the cells of the fish that were immersed in the plasmid containing the gene for β-galactosidase. Thus, the fish immersed in water containing a plasmid encoding a foreign gene for eukaryotic expression take up the plasmid into their cells and express the foreign gene.

EXAMPLE 2

Vaccination of Fish Using Plasmid DNA without Liposomes

DNA vaccine s may not in all cases induce the expression of detectable amounts of proteins or gene products (Ulmer, et al., 1993). For example, Davis et al. in Example 7 of U.S. Pat. No. 5,780,448 stated that fish immersed in a liposome-free solution of expression plasmids containing the gene for luciferase did not express detectable amount of luciferase. The present example, however, demonstrates that aquatic animals may have an immunological response to a DNA vaccine, even if there is not a detectable level of gene product formed. The present example also demonstrates that immersion vaccination is equally as effective as injection vaccination in fish.

The DNA vaccine plasmid constructs for this experiment consisted of pcDNA3.1+(Invtirogen, Inc.) empty plasmid as the control plasmid, and pORF46 as the treatment plasmid. The pORF46 plasmid contains a putative channel catfish virus (CCV) envelope gene.

Channel catfish (*Ictalurus punctatus*) weighing approximately five grams were maintained in 38 liter aquaria at 25 C. The fish were divided into three treatment groups and one negative control group. Each fish in a treatment group received either 50 µg of empty plasmid (pcDNA3.1+) by intramuscular injection, 50 µg of pORF46 by intramuscular injection, or 50 µg of pORF46 per fish by immersion in 200 ml of tank water for 60 minutes with aeration. The fish in the immersion group were vaccinated simultaneously by immersing six fish in 200 ml of tank water containing 300 µg pORF46. All treatment groups were vaccinated three times at 14 day intervals and all fish were challenged by intraperitoneal injection with 1000 $TCID_{50}$ units of CCV ($LD_{80}$) 21 days after the last vaccination.

Seven days after virus challenge, six fish in the unvaccinated control group had died, three fish each in the pORF46 treated groups died, and zero fish in the empty plasmid group died (Table 1). This result suggests that fish simply immersed in a solution of plasmid DNA without liposomes will display increased resistance to viral challenge, equal to the resistance observed in fish injected with the same plasmid construct.

TABLE 1

| Treatment Group | Total Fish | Mortalities at 7 days post challenge | Relative Percent Survival |
| --- | --- | --- | --- |
| No Treatment | 7 | 6 | — |
| pcDNA3.1+ | 5 | 0 | 100% |
| pORF46 Injection | 6 | 3 | 41.7% |
| pORF46 Immersion | 6 | 3 | 41.7% |

EXAMPLE 3

Induction of Nonspecific Immunity

Nonspecific immunity is the first line of host defense, and it is also critical for the efficient induction of an adaptive immune response. DNA vaccines can induce a nonspecific cytotoxic cell response in the mouse model. The unmethylated CpG-like motifs in the plasmid backbone of DNA vaccines are also able to induce nonspecific cytotoxic activity in the channel catfish upon injection of empty plasmid into the muscle (Chitmanat, et al., 1999).

Three channel catfish fingerlings each were immersed in 200 ml of tank water containing either 100 µg, 300 µg, or 500 µg of plasmid DNA (pcDNA3.1+, Invitrogen, Inc.) per fish for 60 minutes with aeration. An unvaccinated control group was immersed in 200 ml of tank water with saline diluent. Sixteen hours after treatment the anterior kidney mononuclear lymphocytes were harvested, partially purified and nonspecific cytotoxic cell killing was measured using HL-60 myeloma cells as targets in a standard $^{51}$Cr release assay. Cytotoxicity was calculated as percent specific lysis. At an effector to target ratio of 80, all plasmid-immersed fish mononuclear cells had approximately a 55% increase in nonspecific killing when compared to the saline immersed control group (Table 2). These findings suggest that the plasmid backbone of DNA vaccines, delivered by liposome-free immersion, can enhance nonspecific cytotoxicity in channel catfish.

TABLE 2

Percent specific lysis of channel catfish nonspecific cytotoxic cells after fish were immersed in plasmid DNA solutions without liposomes.

| | Percent Specific Lysis | | | |
|---|---|---|---|---|
| E:T Ratio | Saline | 100 µg/fish | 300 µg/fish | 500 µg/fish |
| 80 | 18 | 30 | 27 | 28 |
| 40 | 11 | 18 | 16 | 20 |
| 20 | 6 | 10 | 7 | 11 |

The following references are hereby incorporated by reference in their entirety:

Anderson, E. D., D. V. Mourich, and J. C. Leong. 1996a. Gene expression in rainbow trout (*Oncorhynchus mykiss*) following intramuscular injection of DNA. Mol. Mar. Biol. Biotechnol. 5:105–113.

Anderson, E. D., D. Mourich, S. C. Fahrenkrug, S. LaPatra, J. Shepherd, and J. C. Leong. 1996b. Genetic immunization of rainbow trout (*Oncorhynchus mykiss*) against infectious hematopoietic necrosis virus. Mol. Mar. Biol. Biotechnol. 5:114–122.

Boume, N., L. R. Stanberry, D. I. Bernstein, and D. Lew. 1996. DNA immunization against experimental genital herpes simplex virus infection. J. Infect. Dis. 173:800–807.

Bouchard, D. A., H. M. Opitz, B. L. Nicholson, S. Blake, and W. R. Keleher, 1998. Diagnosis of two emerging virus infections in the Bay of Fundy. 23rd Annual Eastern Fish Health Workshop Proceedings 23:4.

Chitmanat, C., L. Jaso-Friedmann, D. Evans, and S. Poet. May 2–5, 1999. Bacterial plasmid DNA induces nonspecific cytotoxic cells of channel catfish (*Ictalurus punctatus*) in vivo. 30th Annual Conference of the International Association for Aquatic Animal Medicine, Boston, Mass.

Cho, J. M., T. H. Lee, H. H. Chung, Y. B. Lee, T. G. Lee, Y. W. Park, and K. B. Han. 1993. Method for the production of salmon growth hormone using a synthetic gene. Lucky, Ltd., Seoul (Rep. Korea). U.S. Pat. No. 5,270,180.

Clark, T. G., and H. W. Dickerson. 1998. Mechanisms of immunity against the parasitic ciliate, *Ichthyopthirius multifiliis*. 23rd Annual Eastern Fish Health Workshop Proceedings. 23:15.

Daheshia, M., N. Kuklin, S. Kanangat, E. Manickan, and B. T. Rouse. 1997. Suppression of ongoing ocular inflammatory disease by topical administration of plasmid DNA encoding IL-10. J. Immunol. 159:1945–1952.

Davis et al. U.S. Pat. No. 5,780,448.

Davison, A. J. and M. D. Davison. 1995. Identification of structural proteins of channel catfish virus by mass spectrometry. Virology 206:1035–1043.

Francis, C. H. and A. E. Ellis. 1994. Production of a lymphokine (macrophage activating factor) by salmon (*Salmo salar*) leucocytes stimulated with outer membrane protein antigens of *Aeromonas salmonicida*. Fish Shellfish. Immunol. 4:489–497.

Fu, T. M., A. Friedman, J. B. Ulmer, M. A. Liu, and J. J. Donnelly. 1997. Protective cellular immunity: cytotoxic T-lymphocyte responses against dominant and recessive epitopes of influenza virus nucleoprotein induced by DNA immunization. J. Virol. 71:2715–2721.

Fynan, E. F., R. G. Webster, D. H. Fuller, J. R. Haynes, J. C. Snatoro, and H. L. Robinson. 1993. DNA vaccines: Protective immunizations by parenteral, mucosal, and gene-gun inoculations. Proc. Natl. Acad. Sci. USA. 90:11478–11482.

Gomez-Chiarri, S. K. Livingston, C. Muro-Cacho, S. Sanders, and R. P. Levine. 1996. Introduction of foreign genes into the tissue of live fish by direct injection and particle bombardment. Dis. Aq. Org. 27:5–12.

Gomez-Chiarri, G. 1998. Development of vaccines against bacterial diseases in salmonid fishes using DNA immunization. 23rd Annual Eastern Fish Health Workshop Proceedings. 23:21.

Hansen, E., K. Fernandes, G. Goldspink, P. Butterworth, P. K. Umeda, and K. C. Chang. 1991. Strong expression of foreign genes following direct injection into fish muscle. FEBS Lett. 290:73–76.

Harvey, D. 1996. Aquaculture Outlook, in: Livestock, Dairy, and Poultry Monthly Report, Economic Research Service, U.S. Department of Agriculture, Washington, D. C.

Heppell, J., E. Tarrab, J. Lecomte, L. Berthiaume, and M. Arella. 1995. Strain variability and localization of important epitopes on the major structural protein (VP2) of infectious pancreatic necrosis virus. Virology. 214:40–49.

Herrmann et al. U.S. Pat. No. 5,620,896.

Hirst, I. D. and A. E. Ellis. 1994. Iron-regulated outer membrane proteins of *Aeromonas salmonicida* are important protective antigens in Atlantic salmon against furunculosis. Fish Shellfish. Immunol. 4:29–45.

Johnsson, J. I. and B. Th. Bjoernsson. 1994. Growth hormone increases growth rate, appetite and dominance in juvenile rainbow trout, *Onchorhynchus mykiss*. Anim. Behav. 48:177–186.

Kodihalli, S., J. R. Hayes, H. L. Robinson, and R. G. Webster. 1997. Cross-protection among lethal H5N2 influenza viruses induced by DNA vaccine to the hemagglutinin. J. Virol. 71:3391–3396.

Mikulski, T. M., L. E. Burnett, and K. G. Burnett. 1998. A Vibrio challenge model to test the impact of water quality on disease susceptibility in shrimp. 23rd Annual Eastern Fish Health Workshop Proceedings. 23:39.

Rahman, A. and N. Maclean. 1992. Fish transgene expression by direct injection into fish muscle. Mol. Mar. Biol. Biotechnol. 1:286–289.

Sambrook et al., *Molecular Cloning, A Laboratory Manual*, 2d, Cold Spring Harbor Laboratory Press (1989).

Siharath, K., R. S. Nishioka, S. S. Madsen, and H. A. Bern. 1995. Regulation of IGF-binding proteins by growth hormone in the striped bass, *Morone saxatilis*. Mol. Mar. Biol. Biotechnol. 4:171–178.

Stanley, L. A. J. S. Hudson, T. E. Schwedler, and S. S. Hayasaka. 1994. Extracellular products associated with virulent and avirulent strains of *Edwardsiella ictaluri* from channel catfish. J. Aquat. Anim. Health. 6:36–43.

Stoskopf, M. K. 1993. Fish Medicine, W. B. Saunders Company, Philadelphia.

Tamai, T., S. Shirahata, T. Noguchi, N. Sato, S. Kimura, and H. Murakami. 1993. Cloning and expression of flatfish (*Paralichthys olivaceus*) interferon cDNA. iochim. Biophys. Acta., 1174:182–186.

Tucker, C. S. and E. H. Robinson. 1990. Channel Catfish Farming Handbook, Van Nostrand Reinhold, New York.

Ulmer, J B., J. J. Donnelly, S. E. Parker, et al. 1993. Heterologous protection ng a viral protein. Science, 259:1745–1749.

What is claimed is:

1. A method for delivering a preselected immunogen into a fin-fish, comprising contacting the fin-fish with an aqueous medium containing an isolated non-infectious, non-integrating polynucleotide that is not in contact with a liposome or lipid carrier, wherein the polynucleotide encodes the immunogen, wherein the polynucleotide is operably linked to a promoter that controls the expression of the polynucleotide in the fin-fish, and wherein the immunogen is expressed in the fin-fish.

2. The method of claim 1 wherein the fin-fish is contacted with the polynucleotide by partially or fully immersing the fin-fish in the medium.

3. The method of claim 1 wherein the fin-fish is contacted with the polynucleotide by spraying the medium onto the fin-fish.

4. The method of claim 1, wherein the medium further contains an uptake enhancing material to facilitate entry of the polynucleotide into cells of the fin-fish, wherein the uptake enhancing material is a non-infectious transfection-facilitating protein or a precipitating agent.

5. The method of claim 1 wherein the polynucleotide is DNA.

6. The method of claim 5, wherein the polynucleotide comprises plasmid DNA.

7. The method of claim 5, wherein the polynucleotide is operably linked to a sequence encoding a signal peptide wherein the signal peptide directs the secretion of a protein, polypeptide or peptide.

8. The method of claim 1, wherein the medium further contains nutrients for the fin-fish.

9. The method of claim 1, wherein the promoter is a cell-specific or tissue-specific promoter.

10. The method of claim 1, where the expression of the polynucleotide is transitory.

11. The method of claim 1, wherein the immunogen is produced for at least one month.

12. The method of claim 1, wherein the immunogen is produced for less than about 10 days.

13. The method of claim 1, wherein the immunogen is expressed in a therapeutic amount.

14. The method of claim 1, wherein the immunogen is a viral protein, a viral peptide, a parasite antigen, a fungal antigen, or a bacterial virulence factor.

15. The method of claim 14, wherein the bacterial virulence factor is an inactive protein toxin.

16. The method of claim 14, wherein the bacterial virulence factor is a fragment of a bacterial toxin.

17. The method of claim 1, wherein the fin-fish is selected from the group consisting of channel catfish, salmonids, sturgeon, flounder, koi, angel fish, gourami, tilapia, hybrid striped bass, arctic char, and carp.

18. A method for inducing an immune response in a fin-fish, comprising contacting the fin-fish with an aqueous medium containing an isolated noninfectious polynucleotide encoding an immunogen, wherein the polynucleotide is operably linked to a promoter that controls the expression of the polynucleotide in the fin-fish, wherein the polynucleotide is present in a sufficient amount so that cellular uptake of the polynucleotide occurs and expression results so as to induce the immune response, and wherein the polynucleotide is not in contact with a liposome or lipid carrier.

19. The method of claim 18, wherein the medium further contains an uptake enhancing material to facilitate entry of the polynucleotide into cells of the fin-fish, wherein the uptake enhancing material is a non-infectious transfection-facilitating protein or a precipitating agent.

20. The method of claim 18, wherein the polynucleotide is DNA.

21. The method of claim 20, wherein the polynucleotide comprises plasmid DNA.

22. The method of claim 18, wherein the fin-fish is selected from the group consisting of channel catfish, salmonids, sturgeon, flounder, koi, angel fish, gourami, tilapia, hybrid striped bass, arctic char, and carp.

23. The method of claim 18, wherein the immunogen is a viral protein, a viral peptide, a parasite antigen, a fungal antigen, or a bacterial virulence factor.

24. The method of claim 23, wherein the bacterial virulence factor is an inactive protein toxin.

25. The method of claim 23, wherein the bacterial virulence factor is a fragment of a bacterial toxin.

26. The method of claim 18, wherein the immune response is protective.

27. The method of claim 18, wherein the medium further comprises an effective amount of an immunological adjuvant.

* * * * *